US012733886B2

(12) United States Patent
Chen et al.

(10) Patent No.: US 12,733,886 B2
(45) Date of Patent: Sep. 15, 2026

(54) METHODS FOR COLLECTING AND PRESENTING PHYSIOLOGICAL SIGNAL DATA AND LOCATION INFORMATION, AND SERVERS AND SYSTEMS IMPLEMENTING THE SAME

(71) Applicant: SyncVision Technology Corporation, New Taipei City (TW)

(72) Inventors: Kuan Hsien Chen, New Taipei City (TW); Chia Hung Wu, New Taipei City (TW); Chung Han Liu, New Taipei City (TW)

(73) Assignee: SYNCVISION TECHNOLOGY CORPORATION, New Taipei City (TW)

( * ) Notice: Subject to any disclaimer, the term of this patent is extended or adjusted under 35 U.S.C. 154(b) by 13 days.

(21) Appl. No.: 18/561,975

(22) PCT Filed: Oct. 12, 2022

(86) PCT No.: PCT/CN2022/124838
§ 371 (c)(1),
(2) Date: Nov. 17, 2023

(87) PCT Pub. No.: WO2023/061402
PCT Pub. Date: Apr. 20, 2023

(65) Prior Publication Data

US 2024/0237953 A1 Jul. 18, 2024

Related U.S. Application Data

(60) Provisional application No. 63/254,715, filed on Oct. 12, 2021.

(51) Int. Cl.

| | |
|---|---|
| ***G06F 3/0481*** | (2022.01) |
| ***A61B 5/00*** | (2006.01) |
| ***G06F 3/0482*** | (2013.01) |

(52) U.S. Cl.
CPC ............ *A61B 5/748* (2013.01); *A61B 5/7425* (2013.01); *A61B 5/7465* (2013.01); *G06F 3/0481* (2013.01); *G06F 3/0482* (2013.01)

(58) Field of Classification Search
None
See application file for complete search history.

(56) References Cited

U.S. PATENT DOCUMENTS 11,817,191 B1 * 11/2023 Naeymi-Rad .......... G06N 3/126
2009/0005649 A1 * 1/2009 Baird ..................... G16H 40/63
600/300

(Continued)

FOREIGN PATENT DOCUMENTS

CN 105706093 A 6/2016
CN 105939658 A 9/2016

(Continued)

OTHER PUBLICATIONS

International Search Report (PCT/ISA/210), issued in PCT/CN2022/124838, mailed Jan. 17, 2023.

*Primary Examiner* — Tuyetlien T Tran
(74) *Attorney, Agent, or Firm* — Birch, Stewart, Kolasch & Birch, LLP

(57) ABSTRACT

Disclosed is a method for collecting and presenting physiological signal data and location information, comprising: receiving physiological signal data; providing a first user interface to receive a first user input, the first user interface including a first representation of human body or a part thereof, and the first user input including a first location of the first representation; converting the first location to a first location information according to a predetermined first mapping relationship; storing the physiological signal data in association with an identification of the first location information; and in response to a request, providing a second user interface, the second user interface including a selection (Continued)

function, which provides a second representation corresponding to the first representation, wherein when a second location in the second representation corresponding to the first location information is selected, the second user interface presents the physiological signal data.

14 Claims, 5 Drawing Sheets

(56) References Cited

U.S. PATENT DOCUMENTS

2010/0017750 A1* 1/2010 Rosenberg ............. A61B 18/14 715/803
2010/0305660 A1* 12/2010 Hegi .................. A61N 1/36071 607/60
2013/0035957 A1* 2/2013 Gossler .................. A61B 5/055 705/3
2014/0038152 A1* 2/2014 Micieli .................. G06Q 10/10 434/267
2014/0062900 A1* 3/2014 Kaula ..................... G16Z 99/00 345/173
2015/0099955 A1* 4/2015 Al-Ali ................ A61B 5/14553 600/364
2017/0112439 A1* 4/2017 Dubin .................... A61B 5/743
2021/0106235 A1* 4/2021 Huang ................. A61B 5/6831
2021/0290060 A1* 9/2021 Ahmed .................. A61B 5/747
2021/0290184 A1* 9/2021 Ahmed ................ A61B 5/7435
2021/0401298 A1* 12/2021 Levi ..................... A61B 5/7225
2022/0386935 A1* 12/2022 Lo .......................... A61B 5/389

FOREIGN PATENT DOCUMENTS

CN 110265132 A 9/2019
CN 112309570 A 2/2021

* cited by examiner

METHODS FOR COLLECTING AND PRESENTING PHYSIOLOGICAL SIGNAL DATA AND LOCATION INFORMATION, AND SERVERS AND SYSTEMS IMPLEMENTING THE SAME

CROSS REFERENCE TO RELATED APPLICATIONS

This application is the National Phase of PCT International Application No. PCT/CN2022/124838, filed on Oct. 12, 2022, which claims priority under 35 U.S.C. 119(e) to U.S. Provisional Application No. 63/254,715, filed on Oct. 12, 2021, all of which are hereby expressly incorporated by reference into the present application.

TECHNOLOGY FIELD

The present invention relates to methods for collecting and presenting physiological signal data, and servers and systems implementing said methods.

BACKGROUND OF THE INVENTION

In current medical and health examinations, if the patient and physician cannot attend real-time examination together, it would be necessary to adopt a way of prior examination and subsequent interpretation. This may often cause the problem that the physician is unable to clearly recognize the location of examination, and thus cannot accurately diagnose. In addition, physicians often lack a convenient interface for recording the collection location when conducting on-site collections, making it difficult to record location information for future reference.

In recent years, in response to various social factors and medical trends, including an aging society and the epidemic of COVID-19, telemedicine has become increasingly common, and the above-discussed issue has evolved from a problem of time gap to a problem of space gap. Although the patient and physician can attend the examination together from different places, but such estranged and remote way of communication may cause the following problems: (i) the physician would like to guide the patient to perform a collection at a specific location, but can only communicate through oral communication, making it difficult for the patient to clearly understand the location where the collection should be performed: (2) when the patient expresses a location of discomfort physical signs, it is difficult to accurately convey the correct information for the physician to understand and perform examinations: (3) similar to the problems of conventional medicine, the current telemedicine system often lacks a convenient recording interface for collection locations, so that it is difficult to store location information for collected data and to reproduce the same, unfavorable for disease record and management.

Therefore, there is still a need to develop a multifunctional examination tool that can be used for remote mobile medical care, which is able to perform visual examination, auscultation, and physiological examinations for common diseases, and renders remote synchronization, to meet the examination needs of most primary medical care.

SUMMARY OF THE INVENTION

In one aspect, the present invention provides a method for collecting and presenting physiological signal data and location information, comprising: receiving physiological signal data: providing a first user interface to receive a first user input, the first user interface including a first representation of human body or a part thereof, and the first user input including a first location of the first representation: converting the first location to a first location information according to a predetermined first mapping relationship: storing the physiological signal data in association with an identification of the first location information; and in response to a request, providing a second user interface, the second user interface including a selection function, which provides a second representation corresponding to the first representation, wherein when a second location in the second representation corresponding to the first location information is selected, the second user interface presents the physiological signal data.

In some embodiments, the method further comprises: in response to the selection of the second location, converting the second location to a second location information according to a predetermined second mapping relationship, accessing physiological signal data in association with an identification of the second location information, and presenting the accessed physiological signal data on the second user interface.

In some embodiments, the second user interface presents the second representation and the physiological signal data in a same screen, and the second representation shows an indication of the second location.

In some embodiments, the first representation includes a plurality of predetermined sub-representations, wherein the first user input includes selecting one of the plurality of predetermined sub-representations.

In some embodiments, the first representation, the second representation or both are a 2D representation, a 3D representation, or a combination thereof.

In some embodiments, the first location information, the second location information or both are a coordinate information, a semantic information, or a combination thereof.

In some embodiments, said method for collecting and presenting physiological signal data and location information further comprises: providing the second user interface on a second user device, and before receiving the physiological signal data, providing on the second user interface a third representation corresponding to the first representation, for receiving a second user input, wherein the second user input includes a third location of the third representation, the third location being a guidance for a human body location for collecting the physiological signal data using a medical inspection/examination device; and providing a menu on the second user interface for receiving a third user input, wherein the menu includes a plurality of inspection/examination items, the third user input including one of the plurality of inspection/examination items.

In some embodiments, the further comprises: corresponding to the third representation, synchronously providing a fourth representation on the first user interface, wherein the fourth representation shows an indication of a fourth location, the fourth location being corresponding to the third location.

In some embodiments, the method further comprises: corresponding to the third representation, controlling the medical inspection/examination device to synchronously show a fourth representation on a display, for guiding a user to collect the physiological signal data using the medical inspection/examination device; and according to the third user input, controlling the medical inspection/examination device to synchronously activate a corresponding sensor for collecting the physiological signal data.

In another aspect, the present invention provides a sever for collecting and presenting physiological signal data and location information, comprising: a processor; a memory, storing instructions executable by the processor: wherein the processor is configured to: receive physiological signal data from a first user device; provide on the first user device a first user interface to receive a first user input, the first user interface including a first representation of human body or a part thereof, and the first user input including a first location of the first representation: convert the first location to a first location information according to a predetermined first mapping relationship: store the physiological signal data in association with an identification of the first location information; and in response to a request, provide a second user interface, the second user interface including a selection function, which provides a second representation corresponding to the first representation, wherein when a second location in the second representation corresponding to the first location information is selected, the second user interface presents the physiological signal data.

In some embodiments, the processor is further configured to: in response to the selection of the second location, convert the second location to a second location information according to a predetermined second mapping relationship, access physiological signal data in association with an identification of the second location information, and present the accessed physiological signal data on the second user interface.

In some embodiments, the second user interface presents the second representation and the physiological signal data in a same screen, and the second representation shows an indication of the second location.

In some embodiments, the second user interface is provided on the first user device.

In some other embodiments, the second user interface is provided on a second user device.

In a further aspect, the present invention provides a system comprising: a sever for collecting and presenting physiological signal data and location information as described above: a computer program product, installed on the first user device, the first user device being communicatively connected to the server; and a medical inspection/examination device, communicatively connected to the first user device.

In a further aspect, the present invention provides a system comprising: a sever for collecting and presenting physiological signal data and location information as described above: a user device, which is the first user device, communicatively connected to the server; and a medical inspection/examination device, communicatively connected to the first user device.

In some embodiments, the physiological signal data is collected by the medical inspection/examination device from a subject. In some embodiments, the computer program product transmits the physiological signal data to the sever.

In some embodiments, the sever provides the first user interface on the first user device via the computer program product.

In some embodiments, the second user interface is provided on the first user device.

In some other embodiments, the second user interface is provided on a second user device.

In some embodiments, the second user interface is provided on the second user device, and the processor is further configured to: before receiving the physiological signal data, provide on the second user interface a third representation corresponding to the first representation, for receiving a second user input, wherein the second user input includes a third location of the third representation, the third location being a guidance for a human body location for collecting the physiological signal data using a medical inspection/examination device; and provide a menu on the second user interface for receiving a third user input, wherein the menu includes a plurality of inspection/examination items, the third user input including one of the plurality of inspection/examination items.

In some embodiments, the processor is further configured to: corresponding to the third representation, synchronously provide a fourth representation on the first user interface, wherein the fourth representation shows an indication of a fourth location, the fourth location being corresponding to the third location.

In some embodiments, the third representation includes a plurality of predetermined sub-representations, wherein the second user input includes selecting one of the plurality of predetermined sub-representations.

In some embodiments, the computer program product controls the medical inspection/examination device to synchronously show a fourth representation on a display, for guiding a user to collect the physiological signal data using the medical inspection/examination device; and according to the third user input, the computer program product controls the medical inspection/examination device to synchronously activate a corresponding sensor for collecting the physiological signal data.

In some embodiments, the server directly controls, or indirectly controls via means known in the art, the medical inspection/examination device to show the fourth representation on a display.

In some embodiments, the physiological signal data collected by the medical inspection/examination device is streamed to the first user device and the second user device, for presenting to the users.

In some embodiments, the second user interface is provided on the second user device, and the processor is further configured to: provide a communication function on each of the first and second user interfaces, allowing users of the first and second user devices to communicate by voice or video.

It is to be understood that both the foregoing general description and the following detailed description are exemplary and explanatory only and are not restrictive of the disclosure.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred.

In the drawings.

Figure 1:
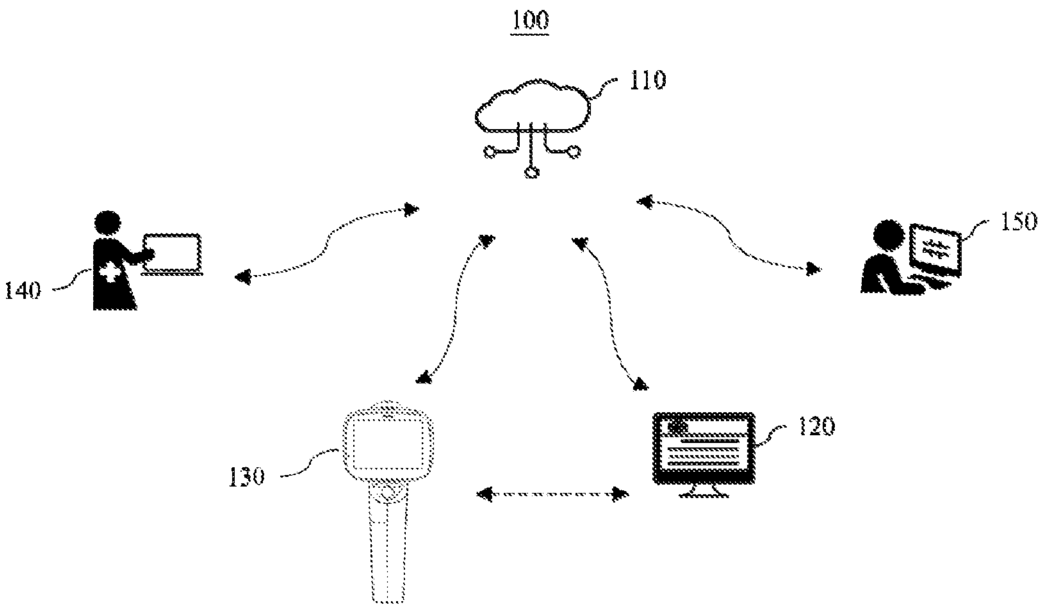
FIG. 1 is a schematic diagram showing a system according to an embodiment of the present invention, which allows users to define and link the relationship between physiological signal itself, location information and virtual human body model image when collecting the physiological signal.

Reference numbers in the drawings; 100 system; 110 server; 120 data processing platform; 130 inspection/examination device; 140 telemedicine caregiver; 150 other users; 200 first user interface; 210 first representation; 212 sub-representation; 300 first user interface; 310 first representation; 320 manual selection.

DETAILED DESCRIPTION OF THE INVENTION

Unless defined otherwise, all technical and scientific terms used herein have the same meanings as is commonly understood by one of skill in the art to which this invention belongs.

The invention will be further described with reference to embodiments of the following examples. However, it should not be understood that the content of the present invention is limited to the following embodiments, and all inventions based on the above content of the present invention are within the scope of the present invention.

Unless otherwise defined, all technical and scientific terms used herein have the same meaning as commonly understood by one of ordinary skill in the art to which this invention belongs.

As used herein, the singular forms “a”, “an”, and “the” include plural referents unless the context clearly dictates otherwise. Thus, for example, reference to “a sample” includes a plurality of such samples and equivalents thereof known to those skilled in the art.

In one aspect, the present invention provides a method for collecting and presenting physiological signal data and location information, comprising:

receiving physiological signal data;

providing a first user interface to receive a first user input, the first user interface including a first representation of human body or a part thereof, and the first user input including a first location of the first representation;

converting the first location to a first location information according to a predetermined first mapping relationship;

storing the physiological signal data in association with an identification of the first location information; and in response to a request, providing a second user interface, the second user interface including a selection function, which provides a second representation corresponding to the first representation, wherein when a second location in the second representation corresponding to the first location information is selected, the second user interface presents the physiological signal data.

A method of the present invention may further comprise the following step: in response to the selection of the second location, converting the second location to a second location information according to a predetermined second mapping relationship, accessing physiological signal data in association with an identification of the second location information, and presenting the accessed physiological signal data on the second user interface.

In a method of the present invention, the order of receiving physiological signal data and providing a first user interface is not limited. In other words, the physiological signal data can be received first and then the first user interface is provided (for a user to specify a location on the body from which the physiological signal data is collected), or a first user interface can be provided first (for a user to pre-specify a body location for performing collection), and then the corresponding physiological signal data is received.

According to the present invention, the physiological signal data may be selected from the group consisting of body temperature data, image data, sound data and a combination thereof. In some embodiments, the image data includes dental image data, eardrum image data, or skin image data. In some embodiments, the sound data includes sound data of lung or sound data of heart.

The term “representation” as used herein is a two-dimensional (2D) representation, a three-dimensional (3D) representation or a combination thereof, of a human body or a portion thereof. Specifically, the representation may be a 2D or 3D model image, which is suitable for display in a user interface, for example, a user interface presented with a touch display. Preferably, the representation can undergo various transformations on the user interface to facilitate viewing and selection. The transformations include, but are not limited to, zooming in, zooming out, translation, and rotation.

According to the present invention, the first user input includes (an indication of) a first location of the first representation. In general, selection function of the second user interface may allow a user to select a predefined location, and/or allow the user to manually select a specific location in the first representation. The first user input may include a predefined location, a manually selected location, or both.

In some embodiments, the first representation includes a plurality of predetermined sub-representations, wherein the first user input includes selecting one of the plurality of predetermined sub-representations. Similarly, the second representation may also include a plurality of predetermined sub-representations, and the selection function of the second user interface allows a user to select one of the plurality of predetermined sub-representations.

Figure 2:
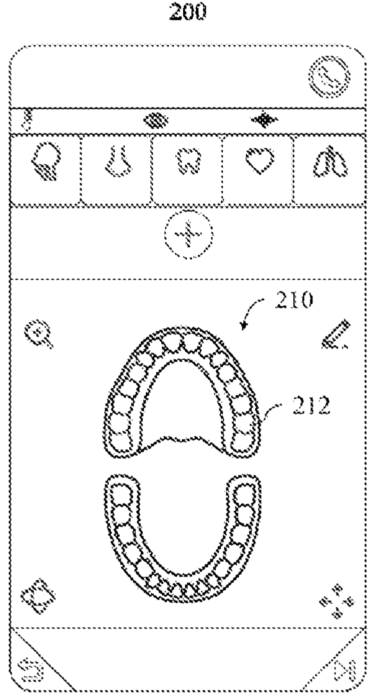
FIG. 2 shows a first user interface according to an embodiment of the present invention, in which the first representation is a tooth model image.

For example, the physiological signal data to be obtained is a tooth image (photo), the first representation is a 2D model image of a human oral cavity (e.g., the first representations 210, 310 in FIGS. 2 and 3), and the plurality of predetermined sub-representations are the 32 teeth in the 2D model image (e.g., sub-representation 212 in FIG. 2). A user can first select one of the 32 teeth in the first user interface (e.g., the first user interfaces 200 and 300 in FIGS. 2 and 3). After selection, the first user interface can display the zoomed-in selected tooth individually. The user can use the first user interface to rotate the zoomed-in 3D model image of the tooth, and further manually select an area on a specific surface of the tooth as a target area for physiological signal data to be obtained. Alternatively, the user may directly select an area on the first representation manually (e.g., manual selection 320 in FIG. 3) as a target area for the physiological signal data to be obtained.

The term "mapping relationship" as used herein refers to one or more location coordinates (i.e., the above-mentioned location information) of the human body or its parts in a first coordinate system and the human body or parts in a second coordinate system. Correspondence between one or more location coordinates represented by its parts. According to the present invention, respective human body (reference) coordinate systems (first coordinate system) and corresponding human body representation coordinate systems (second coordinate system) can be pre-established for different needs (for example, adult men, adult women or children), and The mapping relationship between the two can be calculated accordingly.

After receiving the indication of the first location, the first location is converted into first location information according to the predetermined first mapping relationship. Specifically, the indication of the first location includes or corresponds to one or more location coordinates in the first coordinate system, which can be converted into one or more locations in the second coordinate system using the predetermined first mapping relationship. coordinates, and the first location information includes one or more location coordinates (represented by coordinate information, semantic information, or a combination thereof) in the second coordinate system. The semantic information may be predetermined based on a plurality of predetermined sub-representations of the first representation as described above, and correspond to one or more location coordinates.

Next, the physiological signal data is stored in association with the identification of the first location information. For example, relational database technology is used to store the identification of the physiological signal data and the first location information. The form of "identification" mentioned in this article includes but is not limited to file tag, file name or basic file information (for example, INI file, Exif information).

Subsequently, in response to a request (which can come from the user of the first user interface, or from other people, such as a medical staff), a second user interface is provided. The second user interface includes a selection function that provides a corresponding A second representation of the first representation, wherein when a second location in the second representation corresponding to the first location information is selected, the second user interface presents the physiological signal data for the user or medical practitioner Personnel etc. view or play the physiological signal data.

According to some embodiments of the present invention, the second user interface presents the second representation and the physiological signal data in the same screen. Preferably, the second representation displays an indication of the second location. The indication includes but is not limited to an arrow indication, a bold-line indication and a color indication.

In some embodiments, a list or menu of a plurality pieces of received physiological signal information may also be provided on the second user interface. When a piece of physiological signal data is selected, the second user interface displays the physiological signal data, the second representation, and an indication of the second location.

In some embodiments, the method for collecting and presenting physiological signal data and location information further comprises: providing the second user interface on a second user device, and before receiving the physiological signal data, providing on the second user interface a third representation corresponding to the first representation, for receiving a second user input, wherein the second user input includes a third location of the third representation, the third location being a guidance for a human body location for collecting the physiological signal data using a medical inspection/examination device.

In some embodiments, the method further comprises: providing the second user interface on a second user device, and before receiving the physiological signal data, providing a menu on the second user interface for receiving a third user input, wherein the menu includes a plurality of inspection/examination items, and the third user input includes one of the plurality of inspection/examination items.

In some embodiments, the method further comprises: corresponding to the third representation, synchronously providing a fourth representation on the first user interface, the fourth representation showing an indication of a fourth location, the fourth location being corresponding to the third location.

In some embodiments, the method further comprises: corresponding to the third representation, controlling a medical inspection/examination device to synchronously show the fourth representation on a display for guiding a user to collect the physiological signal data using the medical inspection/examination device.

In some embodiments, the method further comprises: according to the third user input, controlling the medical inspection/examination device to synchronously activate a corresponding sensor for collecting the physiological signal data.

In some embodiments, the second user interface is provided on a second user device, and the physiological signal data collected by the medical inspection/examination device is streamed to the first user device and the second user device for presentation to a user (for example, streaming audio information or video information through an App or web browser).

The present invention also provides a system, which is configured to perform a method as described above.

In addition, a method of the present invention may be performed by a cloud server.

Accordingly, the present invention provides in another aspect a server for collecting and presenting physiological signal data and location information, which comprises:

- a processor; and
- a memory, storing instructions executable by the processor;
- wherein the processor is configured to:
- receive physiological signal data from a first user device;
- provide on the first user device a first user interface to receive a first user input, the first user interface including a first representation of human body or a part thereof, and the first user input including a first location of the first representation;
- convert the first location to a first location information according to a predetermined first mapping relationship;
- store the physiological signal data in association with an identification of the first location information; and
- in response to a request, provide a second user interface, the second user interface including a selection function, which provides a second representation corresponding to the first representation, wherein when a second location in the second representation corresponding to the first location information is selected, the second user interface presents the physiological signal data.

In a further aspect, the present invention provides a system, which comprises:

- a sever for collecting and presenting physiological signal data and location information as described above;
- a computer program product, installed on the first user device, the first user device being communicatively connected to the server; and
- a medical inspection/examination device, communicatively connected to the first user device.

In a further aspect, the present invention provides a system, which comprises:

- a sever for collecting and presenting physiological signal data and location information as described above;
- a user device, which is the first user device, communicatively connected to the server; and
- a medical inspection/examination device, communicatively connected to the first user device.

According to the present invention, the instructions are machine-executable instructions stored in the memory, which when executed by the processor, cause the processor to operate in accordance with embodiments described herein.

The term “user device” as used herein includes, but is not limited to, a smartphone, tablet, laptop, or desktop computer. The computer program product may be a mobile application (App). A user of a user device and/or software product may enter their user ID and password and log in to the computer program product after being authenticated by the server.

The physiological signal data may be collected from a subject, preferably a human subject, by the medical inspection/examination device. The physiological signal data may be first transmitted to and temporarily stored in the first user device, and then the computer program product sends the physiological signal data to the server.

Then, the server stores the physiological signal data in association with an identification of the first location information. In some embodiments, a timestamp of the data or file is used as an identifier or a part thereof. In some embodiments, a user ID as described above is used as an identifier or a part thereof. In some embodiments, an identification may include a timestamp and a user ID.

According to the present invention, the server provides the first user interface on the first user device via the computer program product. A user may use the first user device and the medical inspection/examination device to collect physiological signal data and specify the collection location of the physiological signal data. In some embodiments, the second user interface is provided on the first user device for the user to view or play the collected physiological signal data, and at the same time view the information of the collection location. In some other embodiments, the second user interface is provided on a second user device. The second user device may be operated by, for example, a medical personnel and view or play the collected physiological signal data via the second user interface, and at the same time he or she can view the information of the collection location. In addition, a medical personnel can also communicate with the user through the second user interface.

In some embodiments, the second user interface is provided on the second user device, and the processor is further configured to: before receiving the physiological signal data, provide on the second user interface a third representation corresponding to the first representation, for receiving a second user input, wherein the second user input includes a third location of the third representation, the third location being a guidance for a human body location for collecting the physiological signal data using a medical inspection/examination device. In some embodiments, the third representation includes a plurality of predetermined sub-representations, wherein the second user input includes selecting one of the plurality of predetermined sub-representations.

In some embodiments, the processor is further configured to: before receiving the physiological signal data, provide a fourth representation corresponding to the third representation on the first user interface, the fourth representation showing an indication of a fourth location, wherein the fourth location is corresponding to the third location, for guiding a user to a location where the medical inspection/examination device is used for collection.

The medical inspection/examination device may have a display or display unit. In some embodiments, the software product controls the medical inspection/examination device to show the fourth representation on the display or display unit to guide a user to a collection location. In some other embodiments, the server directly controls or indirectly controls the medical inspection/examination device to show the fourth representation on a display through means known in the art.

In some embodiments, the processor is further configured to: provide the second user interface on a second user device, and before receiving the physiological signal data, provide on the second user interface a third representation corresponding to the first representation, for receiving a second user input, wherein the second user input includes a third location of the third representation, the third location being a guidance for a human body location for collecting the physiological signal data using the medical inspection/examination device.

In some embodiments, the processor is further configured to: provide the second user interface on a second user device, and before receiving the physiological signal data, provide a menu on the second user interface, for receiving a third user input, wherein the menu includes a plurality of inspection/examination items, and the third user input includes one of the plurality of inspection/examination items.

In some embodiments, the processor is further configured to: corresponding to the third representation, synchronously provide a fourth representation on the first user interface, the fourth representation showing an indication of a fourth location, wherein the fourth location is corresponding to the third location.

In some embodiments, the processor is further configured to: corresponding to the third representation, control a medical inspection/examination device to synchronously show the fourth representation on a display, for guiding a user to collect the physiological signal data using the medical inspection/examination device.

In some embodiments, the processor is further configured to: according to the third user input, control the medical inspection/examination device to synchronously activate a corresponding sensor for collecting the physiological signal data.

In some embodiments, the second user interface is provided on the second user device, and the physiological signal data collected by the medical inspection/examination device is streamed to the first user device and the second user device for presentation to a user (for example, streaming audio information or video information through an App or web browser).

In some embodiments, the second user interface is provided on the second user device, and the processor is further configured to: provide a communication function on each of the first and second user interfaces, allowing users of the first and second user devices to communicate by voice or video.

In some embodiments, an inspection system for collecting and reproducing (presenting) physiological signals and location information is provided, including collection data, defining collection locations, and reproducing steps for defining, connecting, and establishing a relationship between collected physiological signals, location information, and virtual human model images. These three pieces of information can be stored independently after being defined. However, once stored, the piece of physiological signal can be reproduced in the system interface when it is retrieved again. For example, by accessing physiological signal information, the visualized location image can be reproduced on the virtual human model image through the linking position information. Such arrangement can be beneficial to detailed records of health management and medical inspection/examination, communication between doctors and patients, tracking and monitoring, and can also provide teaching and training opportunities for doctors and nursing staff.

In some embodiments, also provided is a system allowing defining a collection location for collected data, and the system has a human body model that can visually present locations, and a synchronization module allowing synchronously interactive operations from both remote and local ends.

In addition, it is provided in some embodiments a device for detecting physiological status, which allows a user to define, link and establish a relationship between the following three pieces of information when collecting physiological signals: (A) physiological signal itself (B) location information (C) virtual human body model image, to facilitate generating a visualized location image on a virtual human body model to show a location where physiological signal itself is collected.

Specifically, provided is a remote diagnosis method for collecting and reproducing physiological signal information, including the steps of defining, linking, and establishing a relationship between collected physiological signal data, location information, and a location on a virtual human model image, wherein the location information includes a coordinate information or semantic information; the method comprises the following steps: a user collecting a physiological signal from a body location of a patient, storing and creating a physiological signal tag, and the physiological signal tag corresponds to the collected physiological signal: obtaining a first human body model location inputted by the user, defined in a model location domain through the virtual human body model image, wherein the first human body model location corresponds to the body location: mapping the first human body model location in the model location domain to a reference location domain, to obtain a location information, wherein a mapping manner of the model location domain and the reference location domain includes location domain mapping, axis combination mapping, point mapping, or semantic mapping: storing the physiological signal tag and the location information as a set of associated data; and when needed, calling the set of associated data, mapping the location information to the model location domain, obtaining a second human body model location, presenting the second model location in a virtual human body model image, and simultaneously presenting physiological signals corresponding to the physiological signal tag to the user.

According to an embodiment of the present invention, the coordinate information is established in the following way: in a reference location domain composed of a two-dimensional plane or a three-dimensional space, an axis is defined in each spatial direction: on each axis, based on changes in directional location, a sequence of values with continuity or discontinuity is defined: in the reference location domain, an input defines a location point, which generates corresponding sequence values in each axis; and a coordinate information is obtained by mapping a combination of sequence values in each axis corresponding to the location point.

According to an embodiment of the present invention, the semantic information is established in the following way: in a reference location domain composed of a two-dimensional plane or a three-dimensional space, marking a set of coordinate information composed of a single point or a continuous trajectory using a semantic information, establishing associated semantic data to obtain semantic information that can be accessed and understood in conjunction with the location coordinate information.

According to embodiments of the present invention, the location domain definition is based on the corresponding derivation definition with respect to an absolute area or volume size of the reference location domain and the model location domain, and based on this estimation result, mapping relationship between sequence of numerical values on each axis of the two location domains is defined, and subsequently through the mapping relationship between sequence of numerical values, scale of the sequence is proportionally scaled continuously or discontinuously to establish the correspondence between the two coordinate systems, and based on this correspondence, image position points or image position trajectories are generated on human body model.

According to an embodiment of the present invention, axis combination mapping is to establish correspondence between sequences of numerical values between the reference location domain and the model location domain on each axis. This combination method can be established in a linear, plane, or three-dimensional location domain, in which a correspondence between coordinate sequences of numerical values of each axis can be independent from each other, and there may be different correspondences between each axis.

According to embodiments of the present invention, point mapping establishes independent mapping rules or general principles for each point in the model location domain and the reference location domain to refine or specialize the special mapping relationship.

According to embodiments of the present invention, semantic mapping is to directly map by presenting, zooming in, zooming out, jumping (displacing), or transforming semantic information of the reference location domain to the model location domain.

According to embodiments of the present invention, location information can be stored as a set of associated data with a plurality of physiological signal tags. When needed, one of the physiological signal tags can be selected, and the corresponding collected physiological signal can be presented along with the second model location.

In some embodiments, a system allowing defining a collection location for collected data is provided, and the system has a human body model that can visually present locations, and a synchronization module allowing synchronously interactive operations from both remote and local ends. This design can effectively improve the problems of traditional medicine and telemedicine.

The above-mentioned system is a system for detecting physiological status, which has a human body model that can visually present locations, and a synchronization module allowing synchronously interactive operations from both remote and local ends. The system includes: an inspection/ examination device operable to collect physiological signal from an examined body location of a patient; a data processing module, which defines, links and establishes the relationship between physiological signals, location information and virtual human model images by the method as described above, and generates a set of associated data: a communication module, which can transmit to or obtain the physiological signals, the set of associated data, patient data from a remote server: a synchronization module, which is able to check whether relevant stored information of the inspection/examination device, the remote server, and the connected remote devices is the same, if not, a synchronous transmission is performed to synchronize the data of all devices and servers to the latest.

In one embodiment, the remote server includes a remote digital health care system, including software and cloud layout, which can provide patient medical records, cloud services and communication diagnosis functions, and can interface with other medical service platforms.

In some embodiments, a device for detecting physiological status is provided, which allows the user to define, link and establish the relationship between the following three pieces of information when collecting a physiological signal: (A) physiological signal itself (B) location information (C) virtual human body model image, to facilitate generating a visualized location image on a virtual human body model to show a location where physiological signal collected.

The device has various detection components and data processing/storage functions, including a handle: a display provided on the handle: an image component connected to the display; and a temperature sensor provided on the display for measuring a subject's body temperature: at least one external lens, including a photosensitive component and a sound sensor: a signal component connected to the display, which is connected and shared with the corresponding photosensitive component, temperature sensor or sound sensor. The device also has a data processing module that can receive signals and be used to indicate the corresponding physiological part to be measured; and a communication module that is used to transmit the input physiological measurement records and health data to a remote digital health care system.

In one embodiment, the device includes a temperature sensor.

In one embodiment, the device includes an otoscope or a therapeutic otoscope.

In one embodiment, the device includes a dermatoscope.

In one embodiment, the device includes a nose and throat inspection scope or a rhinoscope.

In one embodiment, the device includes a dental plaque scope, or an intraoral camera.

In one embodiment, the device includes a stethoscope.

In a preferred embodiment, the device includes six detection functions: temperature sensor, electronic stethoscope, otoscope, dermatoscope, nose and throat inspection scope, and dental plaque scope. Using these functions, users can perform remote inspection/examination with connection to remote medical staff through remote diagnosis software for real-time communication and diagnosis.

In addition, in some embodiments, a remote digital healthcare system is also provided. The device of the present invention can utilize a communication module to transmit input physiological measurement records and health data to the remote digital healthcare system. The system includes software and cloud layout, which can provide patient medical records, cloud services and communication diagnosis functions, and can interface with other medical service platforms.

FIG. 1 shows a system 100 according to an embodiment of the present invention, including a server 110, a data processing platform 120 (for example, a mobile device and/or App) and an inspection/examination device 130. The server 110 may also provide a user interface for telemedicine caregivers 140) or other users 150 to enter or receive information. The system 100 allows the user to define, link and establish the relationship between the following three pieces of information when collecting physiological signals: (A) physiological signal (B) location information (C) virtual human body model image, to facilitate generating a visualized location image on a virtual human body model to show a location where physiological signal collected. The relationship between these three pieces of information can be stored independently after being defined. However, once stored, the correlation between these three pieces of information can be reproduced in system interface when accessed again. For example, when a physiological signal is retrieved, through the linked location information visualized location image can be reproduced on a virtual human model image. Such arrangement can be beneficial to detailed records of health management and medical inspection/examination, communication between doctors and patients, tracking and monitoring. The definitions of physiological signals, location information and virtual human model images are as follows:

(A) Physiological signals: Physiological measurement and examination data, which may include visual inspection (image), auscultation (sound), physical signs (data), etc., and do not have a locational meaning.

(B) Location information: A set of data which a user selects by himself/herself, and has a coordinate locational meaning: also, it may include two methods: (B-1) predetermined location and (B-2) manually selected location. The location information is based on coordinate data composed of two axes of a two-dimensional plane or three axes of a three-dimensional space on an absolute coordinate space (I), wherein a set of coordinate data represents a location point. (B-1) The predetermined location is defined by a single semantic information, which corresponds to a specific set of one or more coordinate data. (B-2) generated from a combination of a plurality of coordinate data in a set of continuous coordinate trajectories generated during a manual selection process, wherein combination of the plurality of coordinate data is combined into a coordinate information. Location information can be visualized as a point or trajectory graphic. Methods (B-1) and (B-2) can be used at the same time, causing their data to co-exist and have a combined location information meaning.

(C) Virtual human body model image: It includes a human body image, in combination with an absolute coordinate space (II) where this image is located.

To meet different usage requirements, another (D) altered virtual human body model image may be defined: It includes a human body image, in combination with an absolute coordinate space (III) where this visual image is located, which has coordinate correspondence with (B) location information and (C) virtual human body model image.

Between the absolute coordinate space (I) and the absolute coordinate space (II), the coordinates of the two have a correlation of corresponding locations. That is, after location information (B) is defined using coordinate space (I), its location can be reproduced position in coordinate space (II) through this correlation of corresponding locations, an image of points or trajectory graphic can be generated and displayed on the image of virtual human body model. This method has two possible applications: (i) after the information of (A), (B), and (C) is stored independently, when retrieved later, relationship combination can be used to reproduce graphical positional meaning of (A) on (C); and (ii) if (C) is altered to (D), that is, the original human body image and the absolute coordinate space where this image is located is re-defined and altered into (III), as long as the coordinate correlation between the absolute coordinate space s (I) and (III) can be defined, when retrieving data with respect to (A), the reproduction of graphical locational meaning of (A) on (D) can be achieved by using the definition of (B) location information and the relationship combination.

Methods for defining, linking and establishing relationships between physiological signals itself, location information and virtual human body model image of the system are described below.

1. How to Define (B) Location Information

The location information of the system includes coordinate information and semantic information.

Coordinate information is defined in the following way: in a two-dimensional plane or three-dimensional space (reference location domain), an axis is defined in each spatial direction. On each axis, based on the change of the direction and position, continuous or discontinuous sequences of numerical values are defined. In this space, if a location point is inputted and defined, then this point can generate a corresponding sequence of numerical values for each direction axis, and the coordinate information of this point is obtained by combining sequences of numerical values on each axis corresponding to this point. For example, location point (1) on a two-axis plane can generate coordinate information (axis 1 sequence of numerical values 1, axis 2 sequence of numerical value 1). In addition, location point (2) on a three-axis space can generate coordinate information (axis 1 sequence of numerical values 2, axis 2 sequence of numerical values 2, axis 3 sequence of numerical values 2). The sequences of numerical values of each axis may be arranged in a cross-replacement manner, and it does not necessarily be combined in the order of axis one, axis two, to axis N.

In other words, the coordinate information is based on a location point input. This input generates individual correspondences of continuous or discontinuous sequences of numerical values on multiple axes, and is obtained by combining corresponding sequences of numerical values on part or all of the axes. The axes described in this paragraph would form a two-dimensional plane or three-dimensional space (reference location domain) with an absolute size. Once the coordinate information is generated, it can be considered as a data with spatial location meaning in the two-dimensional plane or three-dimensional space (reference location domain).

Semantic information, also called auxiliary information, is defined in the following way: In the present system, for a coordinate information composed of any set of single points or continuous trajectories in the aforementioned two-dimensional plane or three-dimensional space (reference location domain), it can be annotated using semantic information, which means that in the present system, associated semantic information can be established on a coordinate information to facilitate linked access and understanding.

2. Technical Means for the Mapping Between (B) Location Information and (C) Virtual Human Body Model Image As mentioned above, the (B) position information of a point or a group of points is composed of the corresponding sequences of numerical values on a plurality of axes in a two-dimensional plane or a three-dimensional space (reference location domain). (C) virtual human body model of the present system also has corresponding sequences of numerical values on a plurality of axes in a two-dimensional plane or a three-dimensional space (reference location domain). The technical means for mapping between (B) and (C) include the following four types:

(1) location domain mapping: Perform a deductive definition of correspondence based on the absolute area or volume of the reference location domain and the model location domain, and follow the results of estimation to define the mapping relationship of sequences numerical values on axes between the two location domains. Then, based on this mapping relationship of sequences numerical values, the sequence is continuously or discontinuously scaled in equal proportions to establish the correspondence between the coordinate information of (B) and (C), and based on this correspondence, graphic location points or graphic location trajectories are generated on the human body model. For example, after deductively estimating that the absolute size of the model location domain (C) is twice that of the reference location domain, coordinate information presented as (1,2,4) in the reference location domain can be transformed into (2, 4, 8) in the model location domain and corresponding graphic points or graphic trajectory can be generated.

(2) Axis combination mapping: Establish the correspondence of sequences of numerical values between individual direction axes of the reference location domain and the model location domain. This method may apply to linear, plane, and three-dimensional location domains, and the correspondence of coordinate sequences of numerical values between each axis may be independent of each other, and there may be different correspondences between each axis. The correspondence of this method is not limited to equal proportion scaling of the sequence scale, but may also include mapping methods such as specific range scaling or uneven scaling, specific numerical movement or jumping (displacement), specific calculation formulas, etc. For example, coordinate information presented as (1,2,4) in the reference location domain may be subjected to the definitions of independent relationship between the model location domain (C) and the reference location domain (B) in each axis as follows:

Numerical relationship of the first axis: C=B×2=2

Numerical relationship of the second axis: C=B+5=7

Numerical relationship of the third axis: C=B×(8−B)=16.

Therefore, corresponding coordinates in the model location domain (C) are (2, 7, 16), and the coordinate information can be transformed into (2, 7, 16) in the model location domain and corresponding graphic points or graphic trajectory can be generated.

(3) Point mapping: Independent mapping rules or general principles for each point in the model location domain (C) and the reference location domain (B) are established, to refine or specialize the special mapping relationship, for example:

First axis numerical values: special case single point C:3=B:5, otherwise C=B×2

Second axis numerical values: In specific interval C: 1~3, C=B+10, otherwise C=B×2

Third axis numerical values: C=B (4) Semantic mapping: In principle, semantic information in the reference location domain (B) can be directly presented, zoomed out, zoomed in, jumped, or transformed and be mapping onto the model location domain through methods (1) to (3) mentioned above, for example:

There is a set of associated semantic data (S) at (1,2,4) in the reference location domain (B)

Location in the model location domain (C) of corresponding to the numerical point (1,2,4) in the reference location domain (B) includes (1,2,4), (1,2,5), (1, 2, 6)

Semantic data (S) in the model location domain may be mapping to an expanded range of (1,2,4), (1,2,5) and (1, 2, 6)

3. Technical Means for Mapping Between (B) Location Information and (D) Altered Virtual Human Body Model Image As described above, (B) position information of a point or a group of points is composed of corresponding sequences of numerical values on a plurality of axes in a two-dimensional plane or a three-dimensional space (reference location domain). (D) altered virtual human body model of the system also has a two-dimensional plane or three-dimensional space (model location domain) where it is located, a plurality of axes therein, and corresponding sequences of numerical values on the axes. The technical means for mapping between (B) and (D) include (1) location domain mapping, (2) axis combination mapping, (3) point mapping and (4) semantic mapping. Except for the different corresponding coordinate relationships, the technical means of mapping are basically the same as the technical means for mapping between (B) location information and (C) virtual human body model image.

4. Technical Means for Mapping Between (C) Virtual Human Body Model Image and (D) Altered Virtual Human Body Model Image In the present system, (C) virtual human body model and its coordinate definition space (II) can be changed to (D) altered virtual human body model and its coordinate definition space (III), with the mapping relationship between (II) and (III) defined. After establishing the mapping relationship between (II) and (III) accordingly, the system can automatically simulate and calculate based on the original (B-1) location information, to display and reproduce a graphical location information on the altered virtual human body model and its coordinate definition space (III), equivalent the manner it is reproduced the original virtual human body model and its coordinate definition space (II). The technical means for mapping between (C) and (D) include (1) location domain mapping, (2) axis combination mapping. (3) point mapping and (4) semantic mapping. Except for the different corresponding coordinate relationships, the technical means of mapping are basically the same as the technical means for mapping between (B) location information and (C) virtual human body model image.

By applying the above technical means, a system for inspecting/examining physiological status can be established, the system having a human body model that can visually display locations, and being equipped with a synchronization module allowing synchronously interactive operations from both remote and local ends, to implement a platform with a remote diagnosis communication window, medical care records, and producing real-time testing results in combination with a device.

The testing device used with this platform has a host machine and three functional testing tools, including rapid testing for visual inspection, auscultation and of physiological values, and can be used to examine symptoms in skin, heart, lungs, arteries, abdomen, ear canals, nasal and throat cavity, teeth, body temperature, etc.

EXAMPLES

Example 1. Pre-determined location (B-1) is selected for image signal (A) and displayed/reproduced on an original virtual human body model image (C) to show its graphic locational information As shown in FIG. 2, when a teeth inspection/examination is selected, virtual human body model in the system interface will first perform corresponding screen focusing, zooming, moving, switching, and the presentation of auxiliary information to help a user focus on the target and do the selection of a pre-determined location or a manual selection. The user may select a pre-determined location (B-1), resulting in the generation a set of corresponding location information with coordinate data and semantic labels/tags. This set of coordinates are single point coordinates are associated with the practically collected dental image, and can be displayed or reproduced on the virtual human body model in real time or when retrieved afterwards, generating one or a group of graphical locational information.

Figure 3:
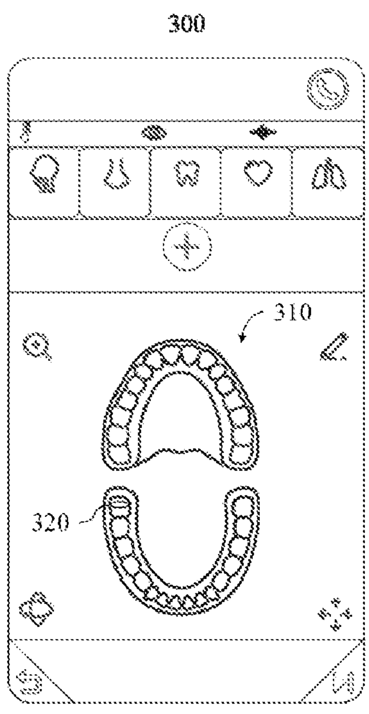
FIG. 3 shows a first user interface according to an embodiment of the present invention, in which the first user input includes a manually selected location.

Example 2: Manually selected location (B-2) is selected for image signal (A) and displayed/reproduced on an original virtual human body model image (C) to show its graphic locational information As shown in FIG. 3, when a teeth inspection/examination is selected, virtual human body model in the system interface will first perform corresponding screen focusing, zooming, moving, switching, and the presentation of auxiliary information to help a user focus on the target and do the selection of a pre-determined location or a manual selection. The user may manually select location (B-2), resulting in the generation of a set of corresponding location information with coordinate data. This set of coordinates is a trajectory formed by a series of continuous coordinates of the manual selection, and is associated with the practically collected dental image, and can be displayed or reproduced on the virtual human body model in real time or when retrieved afterwards, generating one or a group of graphical locational information.

Figure 4:
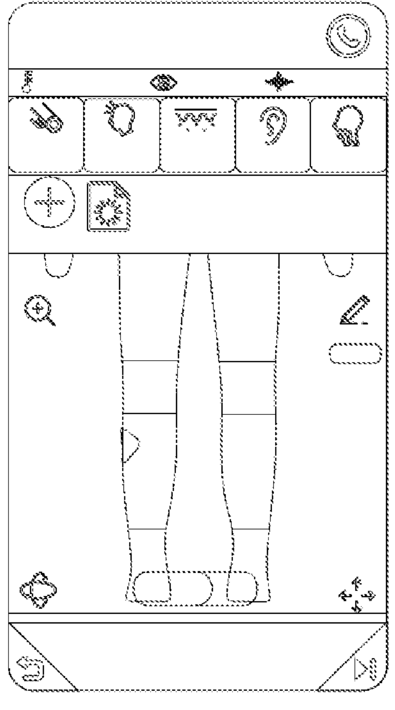
FIG. 4 shows a first user interface according to an embodiment of the present invention, which can be used in specifying a location information of a skin image signal.
Figure 4:
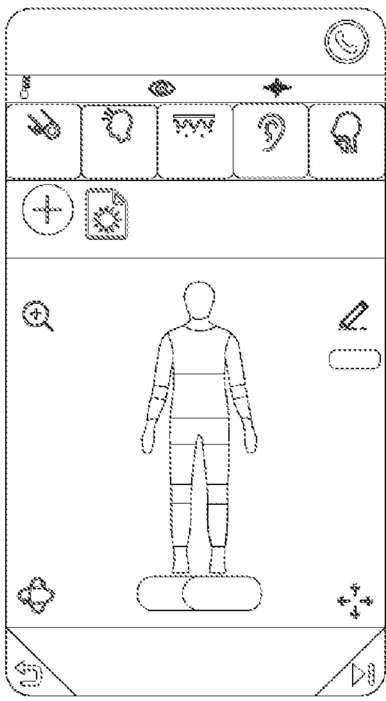

Example 3: Pre-determined location (B-1) is selected for image signal (A) and displayed/reproduced on an altered virtual human body model image (D) to show its graphic locational information As shown in FIG. 4, when a skin inspection/examination is selected, the virtual human model in the system interface will first perform corresponding screen focusing, zooming, moving, switching, and the presentation of auxiliary information to help a user focus on the target and do the selection of a pre-determined location or a manual selection. The user may select a pre-determined location (B-1), resulting in the generation a set of corresponding location information with coordinate data and semantic labels/tags. This set of coordinates are single point coordinates and is associated with the practically collected dental image, and can be displayed or reproduced on the virtual human body model in real time or when retrieved afterwards, generating one or a group of graphical locational information.

In the present system, virtual human body model can be altered to meet different needs, such as enlarging the body to match developmental growth, changing body shape to match individual differences, or working with a specialist physician to change positions and proportions between various points of an organ according to clinical needs. That is, in the present system, an original virtual human body model and its coordinate definition space (II) can be changed to an altered virtual human body model and its coordinate definition space (III), with the mapping relationship between (II) and (III) defined. After establishing the mapping relationship between (II) and (III) accordingly, the system can automatically simulate and calculate based on the original (B-1) location information, to display and reproduce a graphical location information on the altered virtual human body model and its coordinate definition space (III), equivalent the manner it is reproduced the original virtual human body model and its coordinate definition space (II).

Example 4: Manually selected location (B-2) is selected for image signal (A) and displayed/reproduced on an altered virtual human body model image (D) to show its graphic locational information When a teeth inspection/examination is selected, virtual human body model in the system interface will first perform corresponding screen focusing, zooming, moving, switching, and the presentation of auxiliary information to help a user focus on the target and do the selection of a pre-determined location or a manual selection. The user may manually select location (B-2), resulting in the generation of a set of corresponding location information with coordinate data. This set of coordinates is a trajectory formed by a series of continuous coordinates of the manual selection, and is associated with the practically collected dental image, and can be displayed or reproduced on the virtual human body model in real time or when retrieved afterwards, generating one or a group of graphical locational information. If in the future it is required to alter the virtual human body model in the system to meet different needs, for example, enlarging the body to match the growth a child, or replacing a deciduous tooth with a permanent tooth, or changing location of human body image due to organ displacement. That is, in the present system, an original virtual human body model and its coordinate definition space (II) can be changed to an altered virtual human body model and its coordinate definition space (III), with the mapping relationship between (II) and (III) defined. After establishing the mapping relationship between (II) and (III) accordingly, the system can automatically simulate and calculate based on the original (B-1) location information, to display and reproduce a graphical location information on the altered virtual human body model and its coordinate definition space (III), equivalent the manner it is reproduced the original virtual human body model and its coordinate definition space (II).

Figure 5:
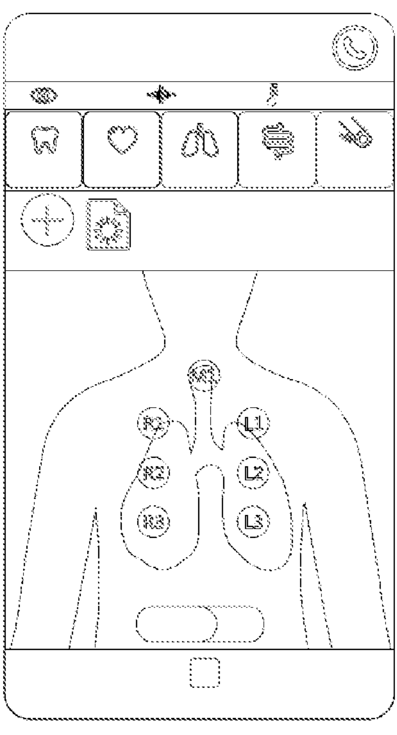
FIG. 5 shows a first user interface according to an embodiment of the present invention, which can be used in specifying a location information of a sound signal of lung.

Example 5: Pre-determined location (B-1) is selected for sound signal (A) and displayed/reproduced on an original virtual human body model image (C) to show its graphic locational information As shown in FIG. 5, when lung sound inspection/examination is selected, the virtual human model in the system interface will first perform corresponding screen focusing, zooming, moving, switching, and the presentation of auxiliary information to help a user focus on the target and do the selection of a pre-determined location or a manual selection. The user may select a pre-determined location (B-1), resulting in the generation a set of corresponding location information with coordinate data and semantic labels/tags. This set of coordinates are single point coordinates and is associated with the practically collected sound signal of lungs, and can be displayed or reproduced on the virtual human body model in real time or when retrieved afterwards, generating one or a group of graphical locational information.

Example 6: Manually selected location (B-2) is selected for sound signal (A) and displayed/reproduced on an original virtual human body model image (C) to show its graphic locational information When an abdomen inspection/examination is selected, virtual human body model in the system interface will first perform corresponding screen focusing, zooming, moving, switching, and the presentation of auxiliary information to help a user focus on the target and do the selection of a pre-determined location or a manual selection. The user may manually select location (B-2), resulting in the generation of a set of corresponding location information with coordinate data. This set of coordinates is a trajectory formed by a series of continuous coordinates of the manual selection, and is associated with the practically collected gastrointestinal sounds, and can be displayed or reproduced on the virtual human body model in real time or when retrieved afterwards, generating one or a group of graphical locational information.

Example 7: Pre-determined location (B-1) is selected for sound signal (A) and displayed/reproduced on an altered virtual human body model image (D) to show its graphic locational information When a femoral artery sound inspection/examination is selected, the virtual human model in the system interface will first perform corresponding screen focusing, zooming, moving, switching, and the presentation of auxiliary information to help a user focus on the target and do the selection of a pre-determined location or a manual selection. The user may select a pre-determined location (B-1), resulting in the generation a set of corresponding location information with coordinate data and semantic labels/tags. This set of coordinates are single point coordinates and is associated with the practically collected femoral artery audio, and can be displayed or reproduced on the virtual human body model in real time or when retrieved afterwards, generating one or a group of graphical locational information.

If in the future it is required to alter the virtual human body model in the system to meet different needs, such as enlarging the body to match developmental growth, changing body shape to match individual differences, or working with a specialist physician to change positions and proportions between various points of an organ according to clinical needs. That is, in the present system, an original virtual human body model and its coordinate definition space (II) can be changed to an altered virtual human body model and its coordinate definition space (III), with the mapping relationship between (II) and (III) defined. After establishing the mapping relationship between (II) and (III) accordingly, the system can automatically simulate and calculate based on the original (B-1) location information, to display and reproduce a graphical location information on the altered virtual human body model and its coordinate definition space (III), equivalent the manner it is reproduced the original virtual human body model and its coordinate definition space (II).

Figure 6:
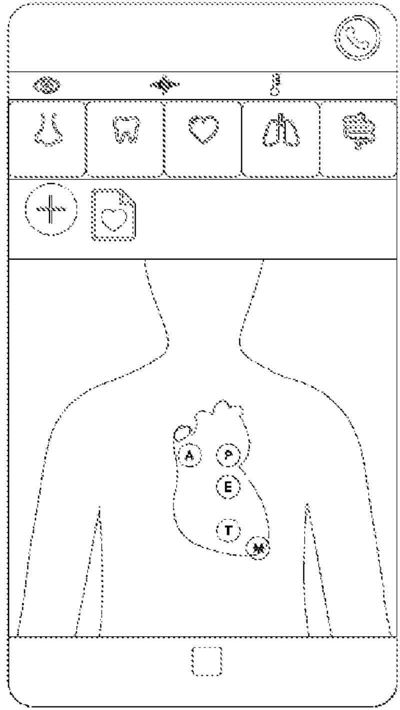
FIG. 6 shows a first user interface according to an embodiment of the present invention, which can be used in specifying a location information of a sound signal of heart.

Example 8: Manually selected location (B-2) is selected for sound signal (A) and displayed/reproduced on an altered virtual human body model image (D) to show its graphic locational information As shown in FIG. 6, when a heart inspection/examination is selected, virtual human body model in the system interface will first perform corresponding screen focusing, zooming, moving, switching, and the presentation of auxiliary information to help a user focus on the target and do the selection of a pre-determined location or a manual selection. The user may manually select location (B-2), resulting in the generation of a set of corresponding location information with coordinate data. This set of coordinates is a trajectory formed by a series of continuous coordinates of the manual selection, and is associated with the practically collected sounds of heart, and can be displayed or reproduced on the virtual human body model in real time or when retrieved afterwards, generating one or a group of graphical locational information. If in the future it is required to alter the virtual human body model in the system to meet different needs, such as working with a specialist physician to change positions and proportions between various points of an organ according to clinical needs. That is, in the present system, an original virtual human body model and its coordinate definition space (II) can be changed to an altered virtual human body model and its coordinate definition space (III), with the mapping relationship between (II) and (III) defined. After establishing the mapping relationship between (II) and (III) accordingly, the system can automatically simulate and calculate based on the original (B-1) or (B-2) location information, to display and reproduce a graphical location information on the altered virtual human body model and its coordinate definition space (III), equivalent the manner it is reproduced the original virtual human body model and its coordinate definition space (II).

Example 9: Both pre-determined location (B-1) and manually selected location (B-2) are selected for image signal (A) and displayed/reproduced on an original virtual human body model image (C) to show its graphic locational information When a teeth inspection/examination is selected, the virtual human model in the system interface will first perform corresponding screen focusing, zooming, moving, switching, and the presentation of auxiliary information to help a user focus on the target and do the selection of a pre-determined location or a manual selection. The user may select a pre-determined location (B-1) and then manually select location (B-2), to be associated with the practically collected tooth image, and can be displayed or reproduced on the virtual human body model in real time or when retrieved afterwards, generating one or a group of graphical locational information. This location marking method that combines (B-1) and (B-2) will have the locational attributes of single point coordinates, continuous coordinate trajectories, and semantic labels/tags at the same time, and have both associatedly displayed characteristics and reproducibility.

Example 10: Both pre-determined location (B-1) and manually selected location (B-2) are selected for image signal (A) and displayed/reproduced on an altered virtual human body model image (D) to show its graphic locational information When a teeth inspection/examination is selected, the virtual human model in the system interface will first perform corresponding screen focusing, zooming, moving, switching, and the presentation of auxiliary information to help a user focus on the target and do the selection of a pre-determined location or a manual selection. The user may select a pre-determined location (B-1) and then manually select location (B-2), to be associated with the practically collected tooth image, and can be displayed or reproduced on the virtual human body model in real time or when retrieved afterwards, generating one or a group of graphical locational information. This location marking method that combines (B-1) and (B-2) will have the locational attributes of single point coordinates, continuous coordinate trajectories, and semantic labels/tags at the same time, and have both associatedly displayed characteristics and reproducibility. If in the future it is required to alter the virtual human body model in the system to meet different needs, for example, enlarging the body to match the growth a child, or replacing a deciduous tooth with a permanent tooth, or changing location of human body image due to organ displacement. That is, in the present system, an original virtual human body model and its coordinate definition space (II) can be changed to an altered virtual human body model and its coordinate definition space (III), with the mapping relationship between (II) and (III) defined. After establishing the mapping relationship between (II) and (III) accordingly, the system can automatically simulate and calculate based on the original (B-1) or (B-2) location information, to display and reproduce a graphical location information on the altered virtual human body model and its coordinate definition space (III), equivalent the manner it is reproduced the original virtual human body model and its coordinate definition space (II).

Figure 7:
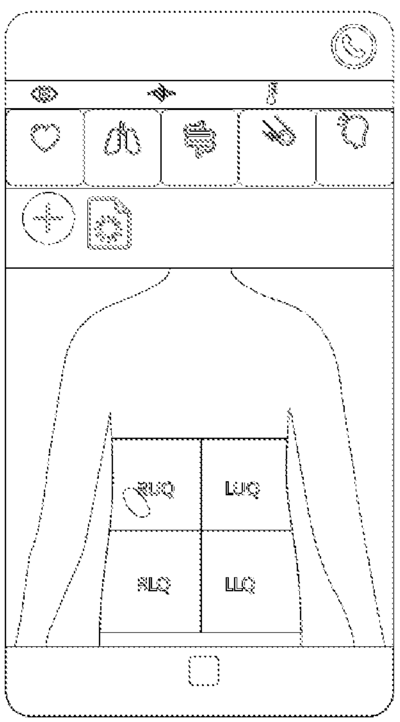
FIG. 7 shows a first user interface according to an embodiment of the present invention, which can be used in specifying a location information of a sound signal of abdomen.
Figure 7:
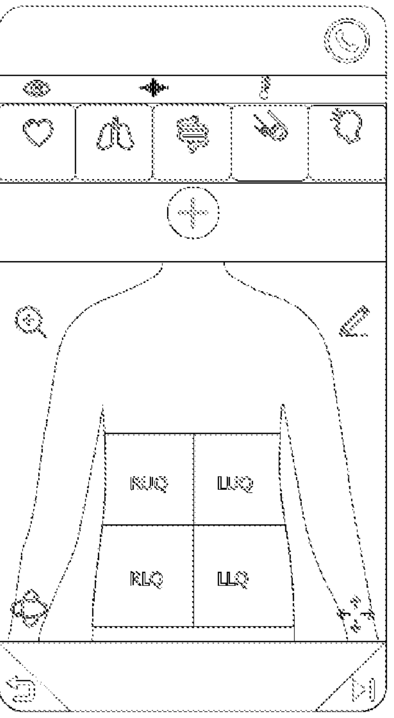

Example 11: Both pre-determined location (B-1) and manually selected location (B-2) are selected for sound signal (A) and displayed/reproduced on an original virtual human body model image (C) to show its graphic locational information As shown in FIG. 7, when an abdomen inspection/examination is selected, virtual human body model in the system interface will first perform corresponding screen focusing, zooming, moving, switching, and the presentation of auxiliary information to help a user focus on the target and do the selection of a pre-determined location or a manual selection. The user may select a pre-determined location (B-1) and then manually select location (B-2), to be associated with the practically collected abdomen audio, and can be displayed or reproduced on the virtual human body model in real time or when retrieved afterwards, generating one or a group of graphical locational information. This location marking method that combines (B-1) and (B-2) will have the locational attributes of single point coordinates, continuous coordinate trajectories, and semantic labels/tags at the same time, and have both associatedly displayed characteristics and reproducibility.

Figure 8:
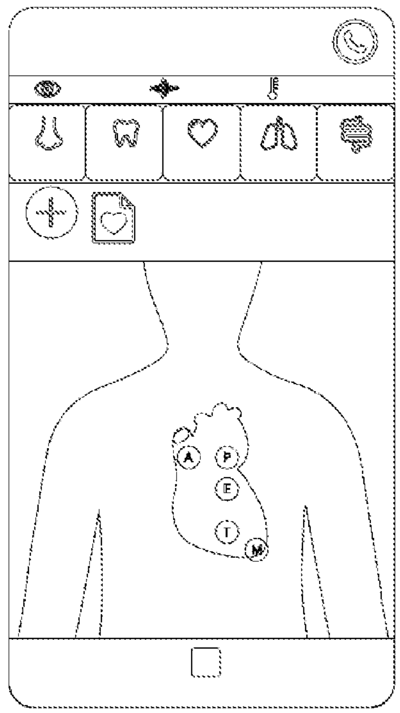
FIG. 8 shows a first user interface according to an embodiment of the present invention, which can be used in specifying a location information of a sound signal of heart.

Example 12: Both pre-determined location (B-1) and manually selected location (B-2) are selected for sound signal (A) and displayed/reproduced on an altered virtual human body model image (D) to show its graphic locational information As shown in FIG. 8, when a heart inspection/examination is selected, the virtual human model in the system interface will first perform corresponding screen focusing, zooming, moving, switching, and the presentation of auxiliary information to help a user focus on the target and do the selection of a pre-determined location or a manual selection. The user may select a pre-determined location (B-1) and then manually select location (B-2), to be associated with the practically collected sounds of heart, and can be displayed or reproduced on the virtual human body model in real time or when retrieved afterwards, generating one or a group of graphical locational information. This location marking method that combines (B-1) and (B-2) will have the locational attributes of single point coordinates, continuous coordinate trajectories, and semantic labels/tags at the same time, and have both associatedly displayed characteristics and reproducibility. If in the future it is required to alter the virtual human body model in the system to meet different needs, such as enlarging the body to match developmental growth, changing body shape to match individual differences, or working with a specialist physician to change positions and proportions between various points of an organ according to clinical need, or replacing four quadrants with nine quadrants. That is, in the present system, an original virtual human body model and its coordinate definition space (II) can be changed to an altered virtual human body model and its coordinate definition space (III), with the mapping relationship between (II) and (III) defined. After establishing the mapping relationship between (II) and (III) accordingly, the system can automatically simulate and calculate based on the original (B-1) or (B-2) location information, to display and reproduce a graphical location information on the altered virtual human body model and its coordinate definition space (III), equivalent the manner it is reproduced the original virtual human body model and its coordinate definition space (II).

Example 13: A platform system that can perform visual inspection, auscultation and physical sign measurement Provided is a platform system that can perform three types of physiological signal detection, which uses several testing tools to perform corresponding detection items, and visualizes physiological locations in a pre-determined or manual way. Examples of its detection steps and items are shown in the table below:

| Step 1. Selecting an inspection function | Step 2. Selecting an inspection item | Step 3-1. (optional) Selecting a location: manually selecting any of the following locations | Step 3-2. (optional) Selecting a location: pre-determined (human body model partitions) | Step 4 (after the selection in Step 3-2) Location coordinates | Data access type |
|---|---|---|---|---|---|
| V. Visual examination | D. Skin and trauma | Whole body | Whole body/ body surface partitions (20 partitions for the front and back respectively) | F1-F20, R1-R20 | Photos/ Videos |
| | E. Ear canal/ eardrum | Head/ear | Head/ear (left, right) | L/R | |
| | N. anterior segment of nasal cavity | Head/nose | Head/nose (left, right) | L/R | |
| | I. Throat/ Intraoral | Head/throat | Head/throat (no partition) | N/A | |
| | T. Teeth | Upper and lower teeth (FDI notation), adults/children | Upper and lower teeth (FDI notation), adults/children | Adults: 11-18, 21-28, 31-38, 41-48 Children: 51-55, 61-65, 71-75, 81-85 | |
| A. Auscultation | H. Heart sounds | Front heart | 5 points on the front | P, A, T, E, M | audio file |
| | L. Lung sounds | Front/back lungs | Front: 7 points Back: 8 points | FR1-FR3, FL1-FL3, FM1, RR1-RR4, RL1-RL4 | |
| | G. Gastrointestinal sounds | Front abdomen | 4 partitions on the front | RUQ, RLQ, LUQ, LLQ | |
| | A. Femoral artery sounds | Front femoral artery | 7 points on the front | Rr, Ri, Rf, A, Lr, Li, Lf | |
| P. Physical sign measurement | F. Forehead temperature | Head/forehead (no partition) | Head/forehead (no partition) | N/A | numerical value |

Figure 9:
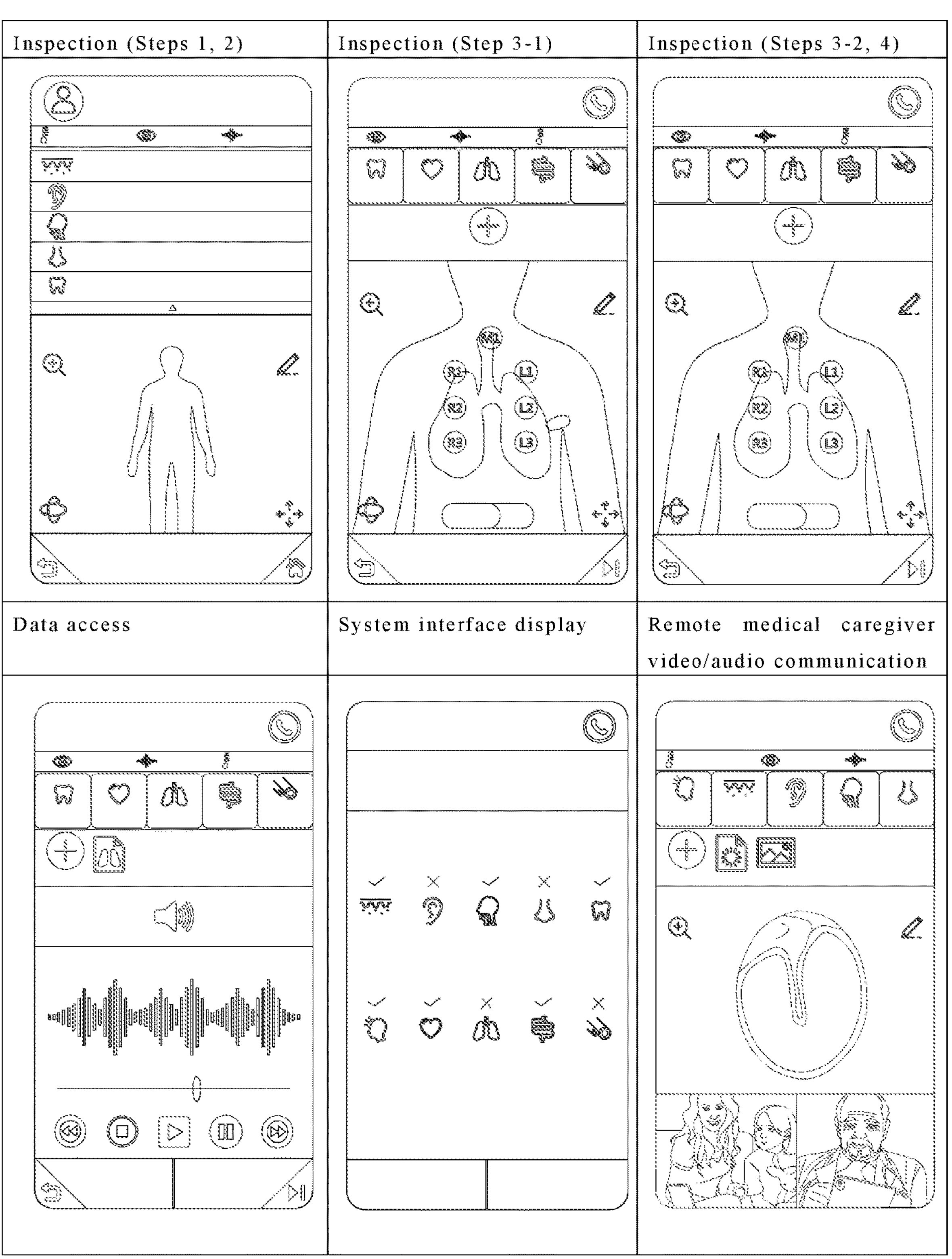
FIG. 9 shows the user interfaces of each step in practical operation of a system for performing visual inspection, auscultation and body temperature measurement according to an embodiment of the present invention.

A practical operation interface of the above platform system is shown in FIG. 9. After inspection/examination, each inspection/examination result has a corresponding code as a data access record. The results can be stored/deleted with confirmation, and comments can be recorded for each inspection/examination result. The inspection/examination results may be displayed in the system interface or exported in a report format. In addition, the above-mentioned inspection/examination process is also connected to a remote location to facilitate video/audio communication between the detection terminal and the remote medical caregiver.

Example 14: Modular server

A server implementing methods of the present invention may include:

A router for communicating with user devices;

Module A: Signal data file storage module, used in defining and storing the collected inspection/examination data itself;

Module B: Location information module, used in defining and storing location information of inspection/examination data;

Module C: Virtual human model image module, used in visual input/display of inspection/examination data locations; and Module D: Correlation and display interface module, used in establishing the relationship between A, B, and C.

Module D is signally or electrically connected to the router, module D is signally or electrically connected to modules A and C, respectively, and module B is signally or electrically connected to modules A and C, respectively. Each of the aforementioned modules can be implemented only by hardware technology, or by hardware technology combined with software technology.

1. Module A: Signal Data File Storage Module

The function of this module is to store the inspection/examination signal itself collected and inputted by an inspection/examination device, the signal including values of visual inspection, audio, and physiology. After each collection, the inspection/examination can first store the data, and then synchronize the data to a user device through a pairing connection (e.g., Bluetooth or near field communication). After storing on the inspection/examination device or synchronizing on the user device, the data is uploaded to a cloud database for storage.

By login a user account and authentication passed using the detection device, user device and (cloud) server, this module can be accessed. All data files that have passed the authentication will be incorporated with an encryption mechanism, and when performing review and editing on the detection device, user device and (cloud) server, the authority must be authenticated and the corresponding decryption mechanism must be implemented. Data is transmitted in encrypted files or packets to ensure that if it is maliciously extracted during the transmission process, the malicious extraction end cannot analyze and use it. Data integrity protection, backup and synchronization: Device-end data is incorporated with an integrity confirmation mechanism, and when transmitted to the client and the cloud, integrity confirmation will be automatically performed. If pairing is interrupted or offline, the data sequence or content is disrupted, or if the data is damaged or missing, integrity synchronization will be performed automatically. The data in the cloud database has an off-site backup mechanism, and if the cloud data is damaged, reverse backup will be automatically performed.

Signal data files can use timestamp as a primary key. For example:

Visual Examination (Images):

Photo: Named by user ID+timestamp, extension: JPG

Video: Named by user ID+timestamp, extension: MP4

Auscultation (Sounds):

PCM: Named by user ID+timestamp, extension: WAV

Temperature (Physiological):

Number: Named by user ID+timestamp, extension: JSON

2. Module B: Location Information Module

The function of this module is to establish location information corresponding to the inspection/examination data. The location information may include the following two types:

(B-1) Predetermined locations: Such location information is based on coordinate data composed of X-axis and Y-axis on an absolute coordinate plane (I), wherein a set of coordinate data represents a location point.

(B-2) Manually selected locations: They are generated from a combination of a plurality of coordinate data in a set of continuous coordinate trajectories generated during a manual selection process. Location information can be visualized as a graphic point or trajectory. The Methods of (B-1) and (B-2) can be used can be used at the same time, so that their data co-exist and have a combined location information meaning.

These two types of location information are created through the "visual input of location information and definition of correspondence" described above. When a user collects inspection/examination data, he/she uses the interface of D to create an intermediate definition of B between A and C: when the user extracts the data, through the correspondence of B, corresponding C can be extracted from A, or corresponding A can be extracted from C.

Location information may use user ID as a primary key and timestamp as a foreign key.

(1) Predetermined Physiological Coordinates can be Named According to Physiological Parts as Follows:

User ID+the following code:

Skin front (SKF), skin back (SKB): numbers 1-18, e.g., SKF01+time stamp.

Ear left (EAL), ear right (EAR): number 00, e.g., EAL 00+time stamp.

Nose left (NOL), nose right (NOR): number 00, e.g., NOR 00+time stamp.

Throat (THR): number 00, e.g., THR 00+time stamp.

Teeth for Adults (TEA), Teeth for Adults (TEC): numbers 1-32, e.g., TEC 01+time stamp.

(2) Manually-Defined Physiological Coordinates can be Named According to Coordinate Data as Follows:

Skin front (SKF), skin back (SKB): coordinate data are composed of a series of continuous X-axis and Y-axis. For example:

SKF_X: 001, 023, 034, 067, 124, 245, 347+timestamp.

SKF_Y: 004, 013, 047, 087, 174, 215, 307+time stamp.

3. Module C: Virtual Human Model Image Module

The function of this module is to create and define appropriate corresponding human body parts for various inspection/examination items, such as specific collection points for heart sounds in clinical settings, or physical locations for collection of common skin problems. The data of each inspection/examination item can be extracted and presented through the interface of D as specified by the user. Specific areas or wireframe blocks can be preset in the drawings, defined as the image corresponding to location information of the predetermined location (B-1), for users to select and review; and the overall image can also be used to allow users to customize a manually selected location (B-2), which includes continuous coordinates, along with the virtual human model image, establish a relative locational relationship through their absolute locations on the coordinate plane, so as to further associate with the signal itself when inputting definitions, and extracting and viewing.

4. Module D: Correlation and Display Interface Module

The function of this module is to define the correspondence between signal data itself and location information, and the requirements for extract the correspondence, to facilitate the definition, extraction, review and editing of the inspection/examination data and location information. In this module, the signal itself, location information, and virtual human model images can be expanded and transformed. For example, the signal itself can be expanded by using different inspection/examination devices to include more signal items. Definitions of location information and virtual human model images can also be expanded to meet practical application requirements. In addition, if one or more of the signal items, location information, and virtual human model images require transformation or change, alterations can be performed with respect to the parts that need to be transformed or changed. After transformation, if the correspondence between A, B and C defined by the correlation module still exists and is correct, the system can use this correspondence to automatically visualize the locational relationship between A and C after the transformation and alteration.

This module can use relational data structures. External parameter input: user ID, timestamp. Internal parameter output: photo or video file path, user physiological coordinates. For example, user ID is used as a primary key and timestamp is used as a foreign key to perform an intersection search. Results of the intersection search are the user's photo or video file path and the user's physiological coordinates. Then the photo or video can be provided in a user interface, and the user's physiological coordinates can be used to search for the user ID. The corresponding virtual human model image is obtained from module C and displayed on the user interface.

5. Input of Visual Location Information and Definition of Correspondence

When collecting the inspection/examination data signal itself, the image of C can be displayed on the interface of D. A user may select a specific image part of C using the interface of D through visual and intuitive operations, and through the correspondence between C and B, B is defined to A: as such, the correspondence between ABC can be established and ABC can be stored independently.

6. Display and Reproduction of Visual Location Information

When reviewing and editing inspection/examination data, a user can perform the following operations on the interface of D: (1) extract, review and edit A on D, and D will simultaneously show the corresponding virtual human model image part in C, or (2) extract, review and edit virtual human model image part in a specific C on D, and D will show the corresponding A simultaneously.

7. Transformation of Virtual Human Model Images

By altering image data of virtual human model images in C, the interface presentation of A visualized in C via B can be re-established to achieve the system's functions relating to transformation.

8. Expansion of Location Information

By altering and expanding the data related to the definition of the predetermined location (B-1) in B, and adding input and presentation options for A and C, the related effects of expanding location information definition of this system can be achieved.

The above method has at least the following advantages:

(1) Convenient for visual observation and switching, data collection, review and communication: users do not need to memorize or imagine the meaning of physiological location of the signal itself. They only need to directly see the system interface to visually and intuitively understand the basis for determining location corresponding to the signal itself. In addition, by switching the upstream location, users can switch to corresponding downstream data of the signal itself: unlike the conventional method of switching the upstream data of the signal itself and then checking the downstream location information, this method is more conducive to fast and correct collection, review and communication regarding inspection/examination data.

(2) The interface content of the virtual human body model image can be transformed: the graphic content of the virtual human body model image can be altered, and the inspection/examination signal itself and location information can be mapped to the altered virtual human body model image. Examples of this application may include: (a) Converting artistic physiological images into images of realistic photography of human body: (b) Converting old physiological images of a same patient into updated physiological images of this same patient, for example, in trunk growth, replacement of deciduous teeth with permanent teeth, and gender transition, this method can be used to transform the original visual image into a new visual image to ensure the latest and most correct visual presentation of the location; (c) Specialized image processing for individual special cases: In special cases such as organ ectopy, abnormal body proportions, abnormal number or shape of limbs, congenital physiological defects, etc., this method can be used to transform image into specialized visual images, to facilitate more accurate data collection, review and communication.

(3) High scalability of location information: For different inspection/examination needs, the definition of predetermined location (B-1) can be expanded to cope with common locations in different situations. It is only required to add new correspondence definitions in Module B (location information module), and the correspondence establishment function of module D can be used to add associated correspondence between location information and virtual human model images, and the expanded position information can be visually presented.

(4) Convenient for data storage and exchange: During storage process, the present system can establish the correspondence between inspection/examination signal itself and the meaning of the location information. The two can be stored independently, so they can be exchanged independently or simultaneously with other databases. Examples of this application may include: (a) The required storage capacity is small: only the signal itself and the location information need to be stored, and the virtual human model image can be used for visual presentation. There is no need to store corresponding images of human physiological locations, and this method effectively reduces the required storage capacity: (b) The required transmission traffic is small: when data is transmitted between devices or systems, or between different users, it does not need to be included in the corresponding pictures of physiological locations of human body, and it is only needed to transmit the signal itself and location information, and use the reproducibility of the virtual human model image to achieve a consistent visual presentation between devices and users, which can effectively reduce the amount of data transmission: (c) It has high exchange compatibility and flexibility with other databases: It can perform highly compatible data exchange with other databases, such as exchanging signal files by simply interfacing with conventional electronic medical records systems: or receiving signal files of other systems for the present system to add location information: or exchanges signal files and location information with other systems, and reproduces or transforms them through their respective visualization image technologies.

Example 15: Inspection/examination example 1 (doctor controls on a cloud platform website)

Doctor end specifies heart sound examination as an inspection/examination item on a cloud platform website (second user interface), and selects and specifies the location to be examined through the human body model image (third representation). The item and location selected by a doctor will be displayed simultaneously on patient end (mobile device App and inspection/examination device). The patient can view the item and location to be inspected/examined through a display of the inspection/examination device. Then, the patient moves the inspection/examination device to the designated inspection/examination location as indicated on the display screen and instructed by the doctor's communication. Meanwhile, the doctor can operate on the cloud platform website and start the streaming of physiological signals, and the inspection/examination device on patient end will respond to a request from the doctor's operation and automatically activate a sensor corresponding to the inspection/examination item, which is an electronic stethoscope in the present example. After activated, real-time audio will be played and streamed on the an electronic stethoscope device, App, and cloud platform website simultaneously for both parties to listen and review.

In addition, the doctor may control the inspection/examination device on the patient end through the cloud platform website to collect physiological signals. In the present example, the recording files and spectrograms of heart sounds are generated and stored, and the generated file will be displayed simultaneously on the inspection/examination device, App and cloud platform website for review by both parties. The generated file can be stored on the server together with the location information for later reproduction or transformation and be presented on the interfaces of the inspection/examination device, App and cloud platform website.

Example 16: Inspection/examination example 2 (controlled by patient end inspection/examination device and App)

A patient may designate skin inspection as an inspection/examination item on an inspection/examination device or an App of mobile device, and select and specify the location to be inspected through the human body model image (first representation) displayed on the App. The item and location selected by the patient will be displayed simultaneously on a doctor end, and a doctor can view the item and location that the patient plans to examine through a cloud platform website. The patient can start the streaming of physiological signals on the inspection/examination device or App. Meanwhile, the inspection/examination device will automatically activate a sensor corresponding to the inspection/examination item, which is a close-focus digital lens designed for skin in the present example. At the same time, the doctor can view the collected physiological signals in real time on the cloud platform website, and the real-time skin images will be displayed simultaneously on the inspection/examination device, App and cloud platform website for both parties to view.

Then, the patient may use the inspection/examination device to collect physiological signals, and in the present example, a video or photo file of the affected skin is generated and stored. The generated file will be displayed simultaneously on the inspection/examination device, App and cloud platform website for review by both parties. In addition, the generated files can be stored on the server together with the location information for later reproduction or transformation, and be presented on the interfaces of the inspection/examination device, App and cloud platform website.

Those of ordinary skill in the art will appreciate that changes may be made to the embodiments described above without departing from the general inventive concept thereof. Therefore, it is to be understood that this invention is not limited to the particular embodiments disclosed, but it is intended to cover modifications within the spirit and scope of this invention as defined by the appended claims.

What is claimed is:

1. A method for collecting and presenting physiological signal data and location information, comprising:

receiving physiological signal data collected by a handheld medical inspection/examination device, the handheld medical inspection/examination device comprising a housing including a handle, a display integrated on the handle, and at least one physiological measurement sensor integrated within the housing;

providing a first user interface to receive a first user input, the first user interface including a first representation of human body or a part thereof, and the first user input including a first location of the first representation indicated by a patient, wherein the first representation is a 2D or 3D model image;

converting the first location to a first location information according to a predetermined first mapping relationship;

storing the physiological signal data in association with an identification of the first location information; and in response to a request, providing a second user interface, the second user interface including a selection function, which provides a second representation corresponding to the first representation, wherein when a second location in the second representation corresponding to the first location information is selected, the second user interface presents the physiological signal data, wherein the method further comprises:

providing the second user interface on a second user device, and before receiving the physiological signal data, providing on the second user interface a third representation corresponding to the first representation, for receiving a second user input, wherein the second user input includes a third location of the third representation, the third location being a guidance for a human body location for collecting the physiological signal data using the medical inspection/examination device;

providing a menu on the second user interface for receiving a third user input, wherein the menu includes a plurality of inspection/examination items, the third user input including one of the plurality of inspection/examination items;

corresponding to the third representation, generating a control signal to cause the integrated display of the handheld medical inspection/examination device to synchronously show a fourth representation at a coordinate on the integrated display corresponding to a coordinate of the third location, to direct a placement of the at least one physiological measurement sensor; and according to the third user input, generating a trigger signal to synchronously activate the at least one physiological measurement sensor corresponding to the selected inspection/examination item for collecting the physiological signal data.

2. The method of claim 1, further comprising:

in response to the selection of the second location, converting the second location to a second location information according to a predetermined second mapping relationship, accessing physiological signal data in association with an identification of the second location information, and presenting the accessed physiological signal data on the second user interface.

3. The method of claim 1, wherein the second user interface presents the second representation and the physiological signal data in a same screen, and the second representation shows an indication of the second location.

4. The method of claim 1, wherein the first representation includes a plurality of predetermined sub-representations, wherein the first user input includes selecting one of the plurality of predetermined sub-representations.

5. The method of claim 1, wherein the first representation, the second representation or both are a 2D representation, a 3D representation, or a combination thereof.

6. The method of claim 1, wherein the first location information, the second location information or both are a coordinate information, a semantic information, or a combination thereof.

7. The method of claim 1, further comprising:

corresponding to the third representation, synchronously providing a fourth representation on the first user interface, wherein the fourth representation shows an indication of a fourth location, the fourth location being corresponding to the third location.

8. A sever for collecting and presenting physiological signal data and location information, comprising:

a processor;

a memory, storing instructions executable by the processor;

wherein the processor is configured to:

receive physiological signal data from a first user device, wherein the physiological signal data are collected by a handheld medical inspection/examination device, the handheld medical inspection/examination device comprising a housing including a handle, a display integrated on the handle, and at least one physiological measurement sensor integrated within the housing;

provide on the first user device a first user interface to receive a first user input, the first user interface including a first representation of human body or a part thereof, and the first user input including a first location of the first representation indicated by a patient, wherein the first representation is a 2D or 3D model image;

convert the first location to a first location information according to a predetermined first mapping relationship;

store the physiological signal data in association with an identification of the first location information; and in response to a request, provide a second user interface, the second user interface including a selection function, which provides a second representation corresponding to the first representation, wherein when a second location in the second representation corresponding to the first location information is selected, the second user interface presents the physiological signal data, wherein the second user interface is provided on a second user device, and the processor is further configured to: before receiving the physiological signal data, provide on the second user interface a third representation corresponding to the first representation, for receiving a second user input, wherein the second user input includes a third location of the third representation, the third location being a guidance for a human body location for collecting the physiological signal data using the medical inspection/examination device; and provide a menu on the second user interface for receiving a third user input, wherein the menu includes a plurality of inspection/examination items, the third user input including one of the plurality of inspection/examination items, and wherein the processor is further configured to communicate with a computer program product, such that: corresponding to the third representation, the computer program product generates a control signal to cause the integrated display of the handheld medical inspection/examination device to synchronously show a fourth representation at a coordinate on the integrated display corresponding to a coordinate of the third location, to direct a placement of the at least one physiological measurement sensor; and according to the third user input, the computer program product generates a trigger signal to synchronously activate the at least one physiological measurement sensor corresponding to the selected inspection/examination item for collecting the physiological signal data.

9. A system comprising:

a sever for collecting and presenting physiological signal data and location information according to claim 8;

a computer program product, installed on the first user device, the first user device being communicatively connected to the server; and a medical inspection/examination device, communicatively connected to the first user device.

10. The system of claim 9, wherein the computer program product transmits the physiological signal data to the sever.

11. The system of claim 9, wherein the sever provides the first user interface on the first user device via the computer program product.

12. The system of claim 9, wherein the processor is further configured to: corresponding to the third representation, synchronously provide a fourth representation on the first user interface, wherein the fourth representation shows an indication of a fourth location, the fourth location being corresponding to the third location.

13. The system of claim 9, wherein the physiological signal data collected by the medical inspection/examination device is streamed to the first user device and the second user device.

14. The system of claim 9, wherein the second user interface is provided on the second user device, and the processor is further configured to: provide a communication function on each of the first and second user interfaces, allowing users of the first and second user devices to communicate by voice or video.

* * * * *